(12) United States Patent
Wei et al.

(10) Patent No.: US 10,083,278 B2
(45) Date of Patent: Sep. 25, 2018

(54) METHOD AND SYSTEM FOR DISPLAYING A TIMING SIGNAL FOR SURGICAL INSTRUMENT INSERTION IN SURGICAL PROCEDURES

(71) Applicant: EDDA TECHNOLOGY, INC., Princeton, NJ (US)

(72) Inventors: Guo-Qing Wei, Plainsboro, NJ (US); Xin Dou, Princeton, NJ (US); Cheng-Chung Liang, West Windsor, NJ (US); Li Fan, Belle Mead, NJ (US); Jian-Zhong Qian, Princeton Junction, NJ (US); Xiaolan Zeng, Princeton, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 898 days.

(21) Appl. No.: 14/619,576

(22) Filed: Feb. 11, 2015

(65) Prior Publication Data

US 2015/0223901 A1    Aug. 13, 2015

Related U.S. Application Data

(60) Provisional application No. 61/938,986, filed on Feb. 12, 2014.

(51) Int. Cl.
*A61B 5/00* (2006.01)
*G06F 19/00* (2018.01)
(Continued)

(52) U.S. Cl.
CPC ............ *G06F 19/321* (2013.01); *A61B 34/20* (2016.02); *G06F 19/3481* (2013.01);
(Continued)

(58) Field of Classification Search
CPC .............................................. A61B 2034/107
See application file for complete search history.

(56) References Cited

U.S. PATENT DOCUMENTS

| 2005/0049478 A1 | 3/2005 | Kuduvalli et al. |
| 2005/0143651 A1 | 6/2005 | Verard et al. |

(Continued)

FOREIGN PATENT DOCUMENTS

EP       1415608 A2     5/2004

OTHER PUBLICATIONS

Extended European Search Report dated Jul. 17, 2017 in European Application 15748648.1.

(Continued)

*Primary Examiner* — Rajeev Siripurapu
(74) *Attorney, Agent, or Firm* — Pillsbury Winthrop Shaw Pittman LLP

(57) ABSTRACT

The present teaching relates to surgical procedure assistance. In one example, a plurality of similarity measures are determined between a first set of positions and a plurality of second sets of positions, respectively. The first set of positions is obtained with respect to a plurality of sensors coupled with a patient in an image captured prior to a surgical procedure. The plurality of second sets of positions are obtained from the plurality of sensors and change in accordance with movement of the patient. A target lesion is segmented in the image captured prior to the surgical procedure to obtain a lesion display object. The lesion display object is duplicated to generate a plurality of lesion display objects. The plurality of lesion display objects are presented on a display screen so that a distance between the plurality of lesion display objects changes in accordance with the plurality of the similarity measures.

22 Claims, 8 Drawing Sheets

(51) Int. Cl.
*A61B 34/20* (2016.01)
*A61B 17/34* (2006.01)
*A61B 34/10* (2016.01)
*A61B 17/00* (2006.01)

(52) U.S. Cl.
CPC . *A61B 17/3403* (2013.01); *A61B 2017/00119* (2013.01); *A61B 2017/00699* (2013.01); *A61B 2034/105* (2016.02); *A61B 2034/107* (2016.02)

(56) References Cited

U.S. PATENT DOCUMENTS

2007/0060799 A1    3/2007   Lyon et al.
2008/0101673 A1    5/2008   Fu et al.
2010/0239144 A1    9/2010   Fichtinger et al.
2012/0029387 A1    2/2012   Wei et al.

OTHER PUBLICATIONS

International Search Report and Written Opinion dated May 18, 2015 in International Application PCT/US2015/015581.

402

404  406

METHOD AND SYSTEM FOR DISPLAYING A TIMING SIGNAL FOR SURGICAL INSTRUMENT INSERTION IN SURGICAL PROCEDURES

CROSS-REFERENCE TO RELATED APPLICATIONS

The present application claims priority to U.S. Provisional Application Ser. No. 61/938,986, filed Feb. 12, 2014, entitled "Graphical User Interface for the Display of a Timing Signal for Needle Insertion in Interventional Procedures," which is incorporated herein by reference in its entirety.

BACKGROUND

Technical Field

The present teaching relates to surgical procedure assistance. More specifically, the present teaching is directed methods, systems, and programming for displaying a timing signal for surgical instrument insertion in surgical procedures.

Discussion of Technical Background

In image-guided interventional procedures, such as needle biopsy or tumor ablation, interventional radiologists place needles or ablation probes based on images taken of the patient immediately before the procedure. For safety reasons, a needle may be inserted stepwise toward the target. Rather a needle may be advanced toward the target step-by-step, and after each needle pass, new images are taken of the patient for verification and/or adjustment of needle position and orientation in order to make the next needle advancement. This process is repeated until the target is reached. This is particular true for lesions located close to critical organs, such as major blood vessels, heart, etc. The imaging modalities used for such needle guidance may include, but not limited to computed tomography (CT), magnetic resonance imaging (MRI), or ultrasound (US).

Since radiologists' decision about needle adjustment and/or needle advancement is based on images taken a few minutes ago, it is important that the patient condition at the time of needle insertion be kept as close as possible to that at image acquisition. Patient movements or breathing may both contribute to the target location changes. While patient movements may be minimized through appropriate measures, such as communications with patients, breathing may need a more quantitative method to control and monitor. Breath holding may not be a viable method since there is no guarantee that the patient may hold the same breath. Besides, some patients may not be able to hold their breath due to health conditions.

With the recent technological advances in magnetic position sensors, methods have been developed that can track needle positions in real-time, so that needle guidance may be performed in a GPS-like manner. From the sensor positions in the images and real-time sensor positions during patient breathing, a timing signal may be extracted that can indicate the best time for needle insertion. This timing signal may be displayed as a curve, similar to the display of an electrocardiogram (EKG) signal on a monitor. Interventional radiologists perform needle insertion or advancement by catching a moment according to the timing-signal display. However, during needle guidance the physicians' visual attention is on the target lesion displayed on the screen. A curve-like display of the timing signal on a different location of the screen is not intuitive and it is difficult for physicians to act upon while at the same time operating the needle. Therefore, there is a need to provide an improved solution to solve the above-mentioned problems.

SUMMARY

The present teaching relates to surgical procedure assistance. More specifically, the present teaching is directed methods, systems, and programming for displaying a timing signal for surgical instrument insertion in surgical procedures.

In one example, a method implemented on a computing device having at least one processor, storage, and a communication platform connected to a network for surgical procedure assistance is disclosed. A plurality of similarity measures are determined between a first set of positions and a plurality of second sets of positions, respectively. The first set of positions is obtained with respect to a plurality of sensors coupled with a patient in an image captured prior to a surgical procedure. The plurality of second sets of positions are obtained from the plurality of sensors and change in accordance with movement of the patient. A target lesion is segmented in the image captured prior to the surgical procedure to obtain a lesion display object. The lesion display object is duplicated to generate a plurality of lesion display objects. The plurality of lesion display objects are presented on a display screen so that a distance between the plurality of lesion display objects changes in accordance with the plurality of the similarity measures.

In another example, a method implemented on a computing device having at least one processor, storage, and a communication platform connected to a network is disclosed. A plurality of similarity measures are determined between a first set of positions and a plurality of second sets of positions, respectively. The first set of positions are obtained with respect to a plurality of sensors coupled with an object in an image captured prior to an operation on the object. The plurality of second sets of positions are obtained from the plurality of sensors and change in accordance with movement of the object. A target object is segmented in the image captured prior to the operation to obtain a target display object. The target display object is duplicated to generate a plurality of target display objects. The plurality of target display objects are presented on a display screen so that a distance between the plurality of target display objects changes in accordance with the plurality of the similarity measures.

In a different example, a system for surgical procedure assistance is disclosed. The system includes a timing signal extraction unit, a target lesion modeling unit, a target lesion duplication unit, and a visualization unit. The timing signal extraction unit is configured to determine a plurality of similarity measures between a first set of positions and a plurality of second sets of positions, respectively. The first set of positions is obtained with respect to a plurality of sensors coupled with a patient in an image captured prior to a surgical procedure. The plurality of second sets of positions are obtained from the plurality of sensors and change in accordance with movement of the patient. The target lesion modeling unit is configured to segment a target lesion in the image captured prior to the surgical procedure to obtain a lesion display object. The target lesion duplication unit is configured to duplicate the lesion display object to generate a plurality of lesion display objects. The visualization unit is configured to present the plurality of lesion display objects on a display screen so that a distance between the plurality of lesion display objects changes in accordance with the plurality of the similarity measures.

Other concepts relate to software for implementing the present teaching on surgical procedure assistance. A software product, in accord with this concept, includes at least one non-transitory machine-readable medium and information carried by the medium. The information carried by the medium may be executable program code data, parameters in association with the executable program code, and/or information related to a user, a request, content, or information related to a social group, etc.

In one example, a non-transitory machine readable medium having information recorded thereon for surgical procedure assistance is disclosed. The recorded information, when read by the machine, causes the machine to perform a series of processes. A plurality of similarity measures are determined between a first set of positions and a plurality of second sets of positions, respectively. The first set of positions is obtained with respect to a plurality of sensors coupled with a patient in an image captured prior to a surgical procedure. The plurality of second sets of positions are obtained from the plurality of sensors and change in accordance with movement of the patient. A target lesion is segmented in the image captured prior to the surgical procedure to obtain a lesion display object. The lesion display object is duplicated to generate a plurality of lesion display objects. The plurality of lesion display objects are presented on a display screen so that a distance between the plurality of lesion display objects changes in accordance with the plurality of the similarity measures.

Additional features will be set forth in part in the description which follows, and in part will become apparent to those skilled in the art upon examination of the following and the accompanying drawings or may be learned by production or operation of the examples. The features of the present teachings may be realized and attained by practice or use of various aspects of the methodologies, instrumentalities and combinations set forth in the detailed examples discussed below.

BRIEF DESCRIPTION OF THE DRAWINGS

The methods, systems, and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, systems, components, and/or circuitry have been described at a relatively high-level, without detail, in order to avoid unnecessarily obscuring aspects of the present teachings.

The present teaching is directed to methods, systems, and programming for displaying a timing signal for surgical instruments (e.g., needles) insertion or advancement in image-guided surgical procedures The system can be realized as a specialized and networked system by utilizing one or more computing devices (e.g., mobile phone, personal computer, etc.) and network communications (wired or wireless). In the following, CT image modality will be used as an exemplary imaging modality. The scope of the present teaching, however, is not limited to the CT imaging modality and can be applied to any known imaging modality such as MRI imaging modality and ultrasound imaging modality.

Figure 1:
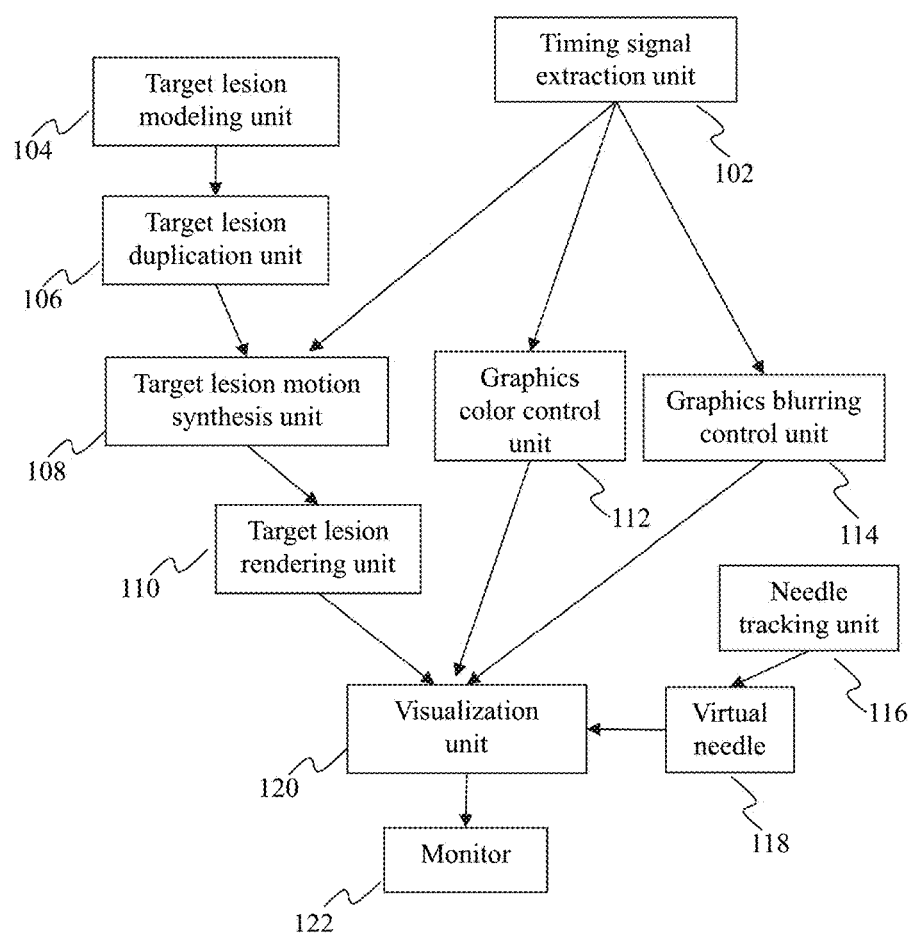
FIG. 1 shows an exemplary system diagram for displaying a timing signal in image-guided surgical procedures according to one embodiment of the present teaching.

FIG. 1 shows an exemplary system 100 for displaying a timing signal for surgical instrument insertion, according to an embodiment of the current teaching. The system 100 includes a timing signal extraction unit 102, a target lesion modeling unit 104, a target lesion duplication unit 106, a target lesion motion synthesis unit 108, a target lesion rendering unit 110, a graphics color control unit 112, a graphics blurring control unit 114, a needle tracking unit 116, and a visualization unit 120. It is understood that although "needle" is described in the present teaching, the surgical instrument insertion timing determination system and method disclosed in the present teaching can be applied to any other suitable instrument used in biopsy and interventional procedures, such as but not limited to probes, knifes, catheters, etc.

The timing signal extraction unit 102 may extract a timing signal based on sensor positions in medical images, such as CT images, and real-time positions of the sensors attached to the patient's body. The timing signal may indicate the optimized timing to insert a surgical instrument, e.g., a needle. During patient breathing or movement, the timing signal is generated in real-time. The target lesion modeling unit 104 may generate a target lesion model. The target lesion duplication unit 106 may duplicate the target lesion in a number of times by a factor, for example, 3. The target lesion motion synthesis unit 108 may synthesize an artificial motion of the target lesions according to the timing signal. The artificial motion may be synthesized in a way that a blurring effect may be generated when the timing is off the optimized timing for surgical instrument insertion. The target lesion rendering unit 110 may generate one or more views of the target lesions in artificial movement. The graphics color control unit 112 may control the display color of one or more graphical objects on a monitor 122 based on the timing signal. The graphics blurring control unit 114 may blur some graphical objects' display based on the timing signal. Both the color and the blurring may be generated in a way that when the timing is off the optimized timing, the color changes and a blurring is introduced. The needle tracking unit 116 may track the position of a sensor attached to a needle. The sensor position may be used to control the movement of a virtual needle 118 or any other surgical instrument, so that their movements are synchronized. The visualization unit 120 may visualize the lesion, graphical objects, and the virtual needle on the monitor 122.

Figure 2:
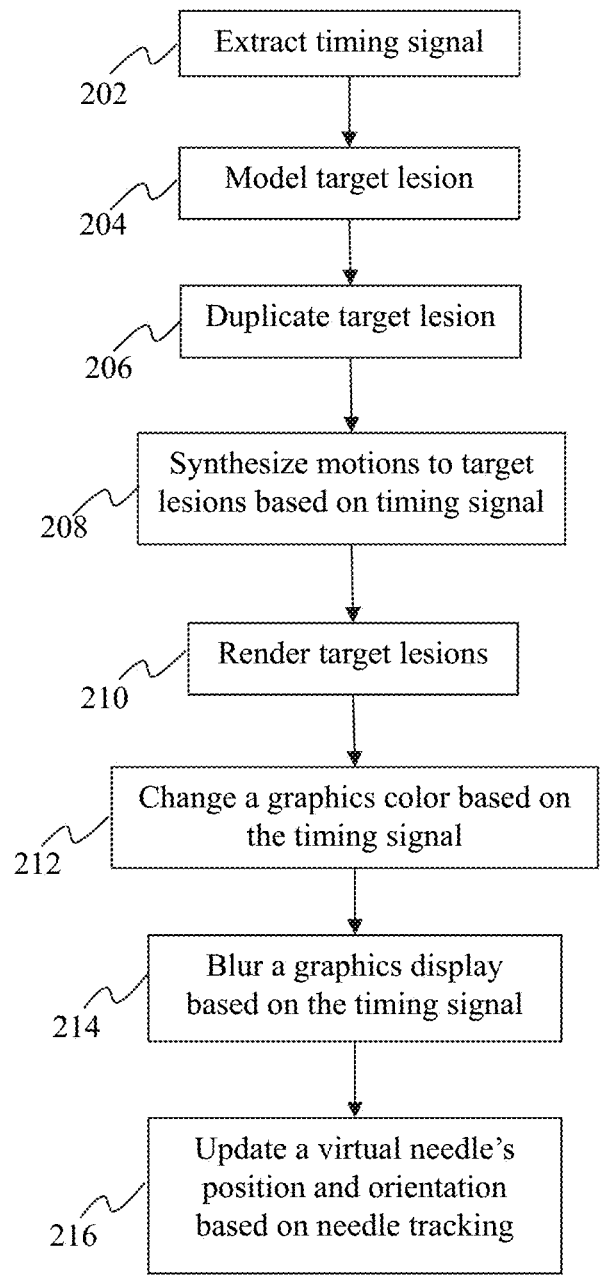
FIG. 2 shows an exemplary flow diagram of a process for displaying a timing signal in image-guided surgical procedures according to one embodiment of the present teaching.
Figure 3:
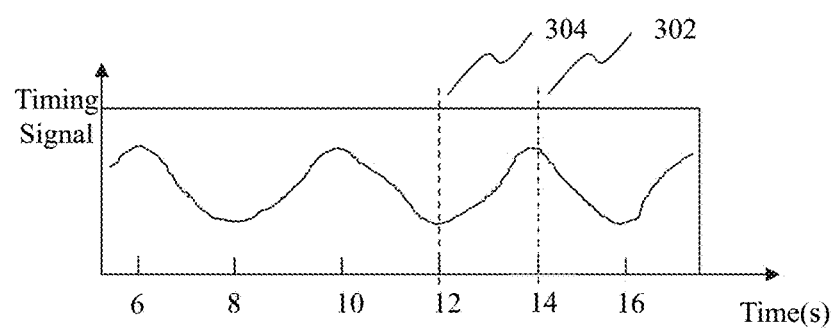
FIG. 3 shows an exemplary timing signal according to one embodiment of the present teaching.

FIG. 2 illustrates an exemplary flowchart for displaying a timing signal, according to one embodiment of the present teaching. At 202, the timing signal may be extracted based on sensor positions in CT images taken before the surgical procedure starts and real-time sensor positions of the same sensors that were attached to the patient's body when the patient was taking the medical images. As one example, the timing signal may be extracted using the method disclosed in U.S. patent application Ser. No. 14/608,267, entitled "Method and System for Determining Optimal Timing for Surgical Instrument Insertion in Image-Guided Surgical Procedures," which is incorporated by reference in its entirety. During patient breathing or movement, a real-time timing signal may be generated to measure similarity measures between the sensor positions from the CT image and the real-time sensor positions from a tracking device. In this embodiment, the CT images of a patient are captured prior to the surgical procedure. A plurality of sensors are coupled with the patient's body. Thus, a first set of positions of the sensors can be extracted from the CT images. As any movement of the patient, e.g., breathing, after taking the CT images may cause the change of the sensors positions, second sets of positions of the same sensors are obtained in real-time from a tracking device. The second sets of real-time sensor positions may be continuously recorded in a time period corresponding to, for example, one or more breathing cycles of the patient to get a full pattern of the sensor positions change. Based on the differences between the first set of positions (static positions taken from CT images) and each of the second set of real-time sensor positions, a series of similarly measures (timing signal) are determined. When the patient breathes to the same condition as that in the CT image, the largest similarity measure (timing signal) is generated. An example of the timing signal is illustrated in FIG. 3. The larger the signal value is, the higher the similarity is between the static sensor positions from the CT image and the real-time sensor positions. So a peak point 302 in FIG. 3 may indicate the optimized timing to insert the surgical instrument, e.g., a needle. It is understood that due to periodicity of breathing, all peaks may be appropriate for surgical instrument insertion. On the contrary, a valley point 304 indicates the least optimized timing to perform a surgical instrument insertion.

Figure 4A:
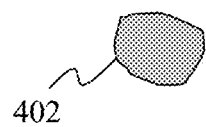
FIG. 4a shows an exemplary lesion model according to one embodiment of the present teaching.
Figure 4B:
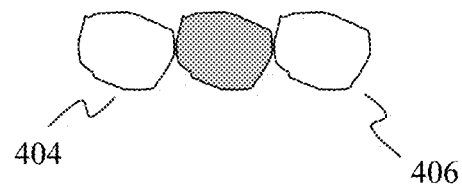
FIG. 4b illustrates the duplication of a lesion model according to one embodiment of the present teaching.
Figure 5:
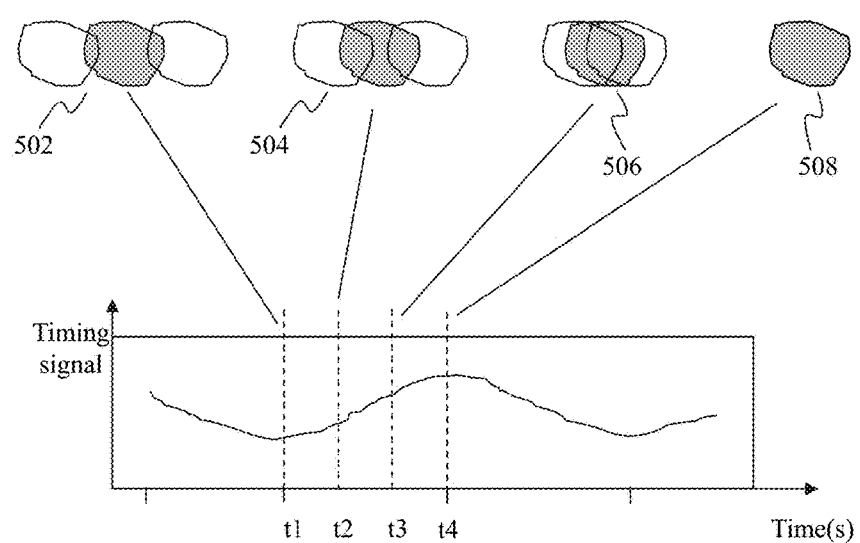
FIG. 5 illustrates an exemplary motion synthesis for multiple lesion models according to one embodiment of the present teaching.

At 204, a target lesion is modeled. The target lesion model (lesion display object) may be obtained through image segmentation techniques that segment the lesion from the CT images. FIG. 4a shows an exemplary lesion model 402. In another embodiment of the present teaching, a spherical display object may be assigned as the lesion model. At 206, the target lesion model (lesion display object) may be duplicated by a certain factor, e.g., 3 times. That's, the lesion model may be copied to generate more than one lesion model. FIG. 4b shows an exemplary duplication of the lesion model 402 to generate two more lesion models 404 and 406. The duplicated lesions may be at the same position as the original lesion or at different positions as shown, for example, in FIG. 4b. At 206, artificial motions may be synthesized for both the original lesion and duplicated lesion models, based on the timing signal. The purpose of producing synthetic motions is to generate a visual effect that when the optimized timing for insertion arrives, the lesion display becomes focused; otherwise it is displayed as blurred. In this way, when physicians look at the lesion display, the visual feedback immediately tells whether it is the time to insert the needle or not. FIG. 5 illustrates an exemplary display of synthetic lesion motion generation. At time t1, the timing signal is the lowest, indicating that it is the least optimized timing to insert a needle. So the synthetic motion may move the lesion models to the furthest apart (502). In this embodiment, the original lesion mode (shaded) may not move, whereas the duplicated ones may move. At times t2 and t3, as the timing signal rises, the duplicated lesions may move closer to the original lesion (504 and 506). At the time t4 of the highest signal level, the duplicate lesions may move to overlap completely with the original lesion (508). That is, the distance between the multiple lesion models (lesion display objects) changes in accordance with the series of similarity measures (timing signal). The distance may decrease as the similarity measure increases, and the multiple lesion display objects overlap with each other at a time with respect to the largest one of the series of similarity measures. Through the above synthetic movement to the duplicated lesions, physicians may know exactly when is the time to perform the needle insertion without having to look at somewhere else to interpret the timing signal to make such a decision. At 210, the lesions may be rendered to generate one or more views on the monitor 122. In one embodiment, a local view from the surgical instrument, e.g., the needle tip may be generated. In this view, when lesion is at the center of the viewport, it indicates that the needle is directed toward the lesion. So navigating the needle using local view may give a better control of the needle. In another embodiment, a global view may be generated. A global view may be preferred when it is needed to view the global spatial relationship between the needle, the lesion, and any other anatomical structures.

Figure 6A:
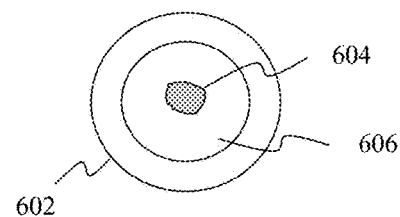
FIG. 6a shows an exemplary viewport from the needle tip according to one embodiment of the present teaching.
Figure 6B:
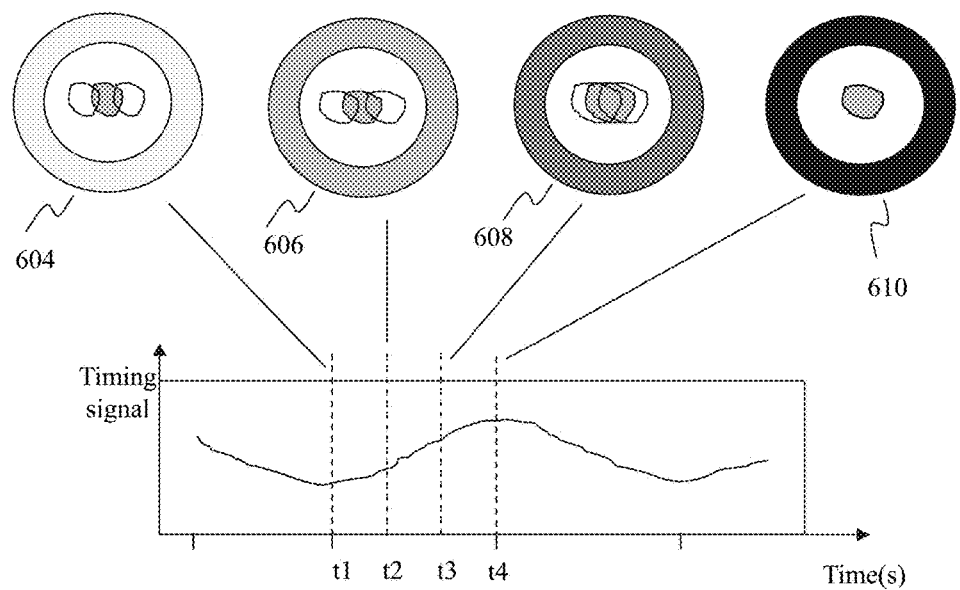
FIG. 6b illustrates exemplary color changes of a viewport from the needle tip according to one embodiment of the present teaching.

At 212, the timing signal may be used to control the color/grayscale of a graphical object. The graphical object may be a ring-shaped viewport in the local view from the surgical instrument, e.g., the needle tip. FIG. 6a illustrates a viewport 602 where the lesion 604 is centered, indicating that the lesion target is aimed at the center by the needle. The area 606 is the viewing area of the local view from the needle. The lesion display objects are presented simultaneously with the ring-shape object (viewport) and are inside the ring-shape object (viewport). The viewport's color/grayscale may be changed according to the timing signal, as illustrated in FIG. 6b. A light color may be displayed at time t1, which is the least optimized timing for needle insertion (604). At times t1 and t2, darker colors may be used to display the view port (606 and 608). At time t4 (the optimized timing), a black color may be used to display the viewport (610). So the color/grayscale change on the viewport corresponds to the timing signal change (the series of similarity measures). The color/grayscale change may be combined with the synthetic motion of duplicated lesions, as shown in FIG. 6b, or may be used separately in other examples.

Figure 7:
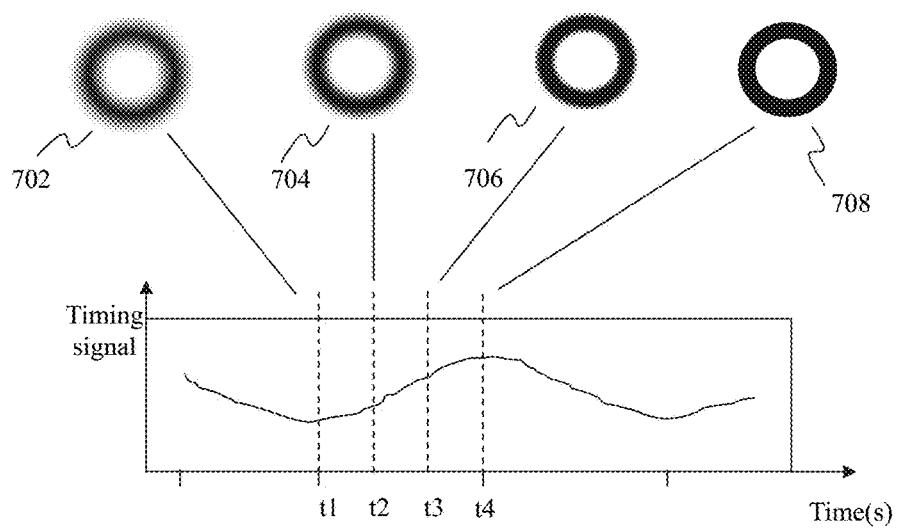
FIG. 7 illustrates exemplary blurring of a viewport from the needle tip according to one embodiment of the present teaching.

At 214, the timing signal may be used to change the blurriness of a graphic object. In one embodiment, the edges of the viewport 602 may be blurred as shown in FIG. 7. At the worst time t1 for needle insertion, the edge of the viewport is mostly blurred to obtain a blurred viewport 702.

As the time approaches to time t4 (the optimized timing), the edge becomes clearer (704 and 706). At time t4 (the optimized timing), there is no blurring of the viewport (708). The blurring of a graphic object may be combined with the synthetic lesion motion approach and/or the color/grayscale control approach or may be used separately. Although only color/grayscale and blurriness changes are mentioned in the embodiments above, it is understood that any visual characteristic associated with the graphic object may change in accordance with the plurality of the similarity measures (timing signal).

Alternatively, a threshold may be applied to the timing signal, so that when the signal (corresponding to any one of the similarity measures) is below the threshold, a warning, e.g., a graphic warning pattern, may be displayed on the monitor 122. When the signal (corresponding to any one of the similarity measures) is above the threshold, the warning is replaced.

At 216, the virtual needle's pose (position and orientation) may be updated based on pose (position and orientation) changes of a sensor attached to the actual needle. So when physicians operate to aim the target lesion, the changes of the actual needle's pose (position and orientation) may be reflected to that of the virtual needle. After the target lesion is aimed, physicians may perform the needle insertion or needle advancement based on the display of the timing signal as described above.

To implement various modules, units, and their functionalities described in the present disclosure, computer hardware platforms may be used as the hardware platform(s) for one or more of the elements described herein (e.g., the system 100 described with respect to FIGS. 1-7). The hardware elements, operating systems and programming languages of such computers are conventional in nature, and it is presumed that those skilled in the art are adequately familiar therewith to adapt those technologies to surgical procedure assistance as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 8:
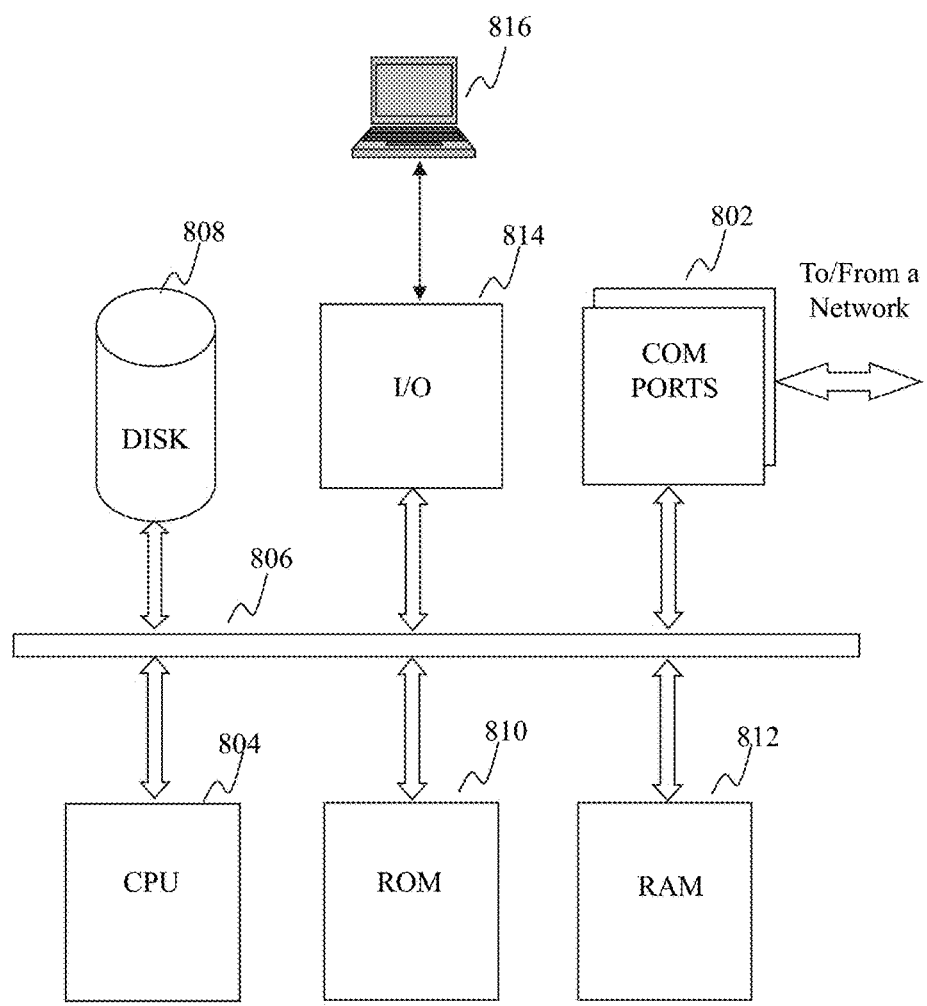
FIG. 8 depicts the architecture of a computer which can be used to implement a specialized system incorporating the present teaching.

FIG. 8 depicts the architecture of a computing device which can be used to realize a specialized system implementing the present teaching. Such a specialized system incorporating the present teaching has a functional block diagram illustration of a hardware platform which includes user interface elements. The computer may be a general purpose computer or a special purpose computer. Both can be used to implement a specialized system for the present teaching. This computer 800 may be used to implement any component of surgical procedure assistance techniques, as described herein. For example, the system 100 may be implemented on a computer such as computer 800, via its hardware, software program, firmware, or a combination thereof. Although only one such computer is shown, for convenience, the computer functions relating to needle guidance as described herein may be implemented in a distributed fashion on a number of similar platforms, to distribute the processing load.

The computer 800, for example, includes COM ports 802 connected to and from a network connected thereto to facilitate data communications. The computer 800 also includes a central processing unit (CPU) 804, in the form of one or more processors, for executing program instructions. The exemplary computer platform includes an internal communication bus 806, program storage and data storage of different forms, e.g., disk 808, read only memory (ROM) 810, or random access memory (RAM) 812, for various data files to be processed and/or communicated by the computer, as well as possibly program instructions to be executed by the CPU 804. The computer 800 also includes an I/O component 814, supporting input/output flows between the computer and other components therein such as user interface elements 816. The computer 800 may also receive programming and data via network communications.

Hence, aspects of the methods of surgical procedure assistance and/or other processes, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer of a search engine operator into the hardware platform(s) of a computing environment or other system implementing a computing environment or similar functionalities in connection with user interest inference. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution—e.g., an installation on an existing server. In addition, the surgical procedure assistance system as disclosed herein may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. A method, implemented on a computing device having at least one processor, storage, and a communication platform capable of connecting to a network for surgical procedure assistance, comprising:
    determining a plurality of similarity measures between a first set of positions and a plurality of second sets of positions, respectively, wherein the first set of positions is obtained with respect to a plurality of sensors configured to be coupled with a patient, in an image captured prior to a surgical procedure, and the plurality of second sets of positions are obtained from the plurality of sensors and change in accordance with movement of the patient;
    segmenting a target lesion in the image captured prior to the surgical procedure to obtain a lesion display object;
    duplicating the lesion display object to generate a plurality of lesion display objects; and
    presenting the plurality of lesion display objects on a display screen so that a distance between the plurality of lesion display objects changes in accordance with the plurality of the similarity measures.

2. The method of claim 1, wherein the distance between the plurality of lesion display objects decreases as the similarity measure increases.

3. The method of claim 1, wherein the plurality of lesion display objects overlap with each other at a time with respect to a largest one of the plurality of the similarity measures.

4. The method of claim 1, further comprising:
    presenting a graphic object on the display screen so that at least one visual characteristic associated with the graphic object changes in accordance with the plurality of similarity measures.

5. The method of claim 4, wherein the at least one visual characteristic includes at least one of color, blurriness, and grayscale.

6. The method of claim 4, wherein the graphic object includes a ring-shape object corresponding to a viewport from a surgical instrument used in the surgical procedure.

7. The method of claim 4, wherein the plurality of lesion display objects and the graphic object are presented simultaneously on the display screen.

8. The method of claim 1, further comprising:
    providing a warning when any one of the plurality of similarity measures is below a threshold.

9. The method of claim 1, wherein the plurality of second sets of positions are obtained in a time period corresponding to one or more breathing cycles of the patient.

10. The method of claim 6, wherein the plurality of lesion display objects are presented inside the ring-shape object.

11. A system for surgical procedure assistance, comprising:
    a timing signal extraction unit configured to determine a plurality of similarity measures between a first set of positions and a plurality of second sets of positions, respectively, wherein the first set of positions is obtained with respect to a plurality of sensors configured to be coupled with a patient, in an image captured prior to a surgical procedure, and the plurality of second sets of positions are obtained from the plurality of sensors and change in accordance with movement of the patient;
    a target lesion modeling unit configured to segment a target lesion in the image captured prior to the surgical procedure to obtain a lesion display object;
    a target lesion duplication unit configured to duplicate the lesion display object to generate a plurality of lesion display objects; and
    a visualization unit configured to present the plurality of lesion display objects on a display screen so that a distance between the plurality of lesion display objects changes in accordance with the plurality of similarity measures.

12. The system of claim 11, wherein the distance between the plurality of lesion display objects decreases as the similarity measure increases.

13. The system of claim 11, wherein the plurality of lesion display objects overlap with each other at a time with respect to a largest one of the plurality of the similarity measures.

14. The system of claim 11, wherein the visualization unit is further configured to present a graphic object on the display screen so that at least one visual characteristic associated with the graphic object changes in accordance with the plurality of the similarity measures.

15. The system of claim 14, wherein the at least one visual characteristic includes at least one of color, blurriness, and grayscale.

16. The system of claim 14, wherein the graphic object includes a ring-shape object corresponding to a viewport from a surgical instrument used in the surgical procedure.

17. The system of claim 14, wherein the plurality of lesion display objects and the graphic object are presented simultaneously on the display screen.

18. The system of claim 11, wherein the visualization unit is further configured to provide a warning when any one of the plurality of similarity measures is below a threshold.

19. The system of claim 11, wherein the plurality of second sets of positions are obtained in a time period corresponding to one or more breathing cycles of the patient.

20. The system of claim 16, wherein the plurality of lesion display objects are presented inside the ring-shape object.

21. A non-transitory machine readable medium having information recorded thereon for surgical procedure assistance, wherein the information, when read by a machine, causes the machine to perform the steps of:

determining a plurality of similarity measures between a first set of positions and a plurality of second sets of positions, respectively, wherein the first set of positions is obtained with respect to a plurality of sensors configured to be coupled with a patient, in an image captured prior to a surgical procedure, and the plurality of second sets of positions are obtained from the plurality of sensors and change in accordance with movement of the patient;

segmenting a target lesion in the image captured prior to the surgical procedure to obtain a lesion display object;

duplicating the lesion display object to generate a plurality of lesion display objects; and presenting the plurality of lesion display objects on a display screen so that a distance between the plurality of lesion display objects changes in accordance with the plurality of the similarity measures.

22. A method, implemented on a computing device having at least one processor, storage, and a communication platform capable of connecting to a network, comprising:

determining a plurality of similarity measures between a first set of positions and a plurality of second sets of positions, respectively, wherein the first set of positions are obtained with respect to a plurality of sensors configured to be coupled with an object, in an image captured prior to an operation on the object, and the plurality of second sets of positions are obtained from the plurality of sensors and change in accordance with movement of the object;

segmenting a target object in the image captured prior to the operation to obtain a target display object;

duplicating the target display object to generate a plurality of target display objects; and presenting the plurality of target display objects on a display screen so that a distance between the plurality of target display objects changes in accordance with the plurality of similarity measures.

* * * * *